US00PP33557P3

(12) United States Plant Patent
Snijder

(10) Patent No.: US PP33,557 P3
(45) Date of Patent: Oct. 12, 2021

(54) ***PELARGONIUM* PLANT NAMED 'PECZ0020'**

(50) Latin Name: ***Pelargonium* x *hortorum***
Varietal Denomination: PECZ0020

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/924,253

(22) Filed: Jul. 9, 2020

(65) Prior Publication Data

US 2021/0243931 P1 Aug. 5, 2021

(30) Foreign Application Priority Data

Feb. 3, 2020 (QZ) ..... PBR 2020/0358

(51) Int. Cl.
*A01H 5/02* (2018.01)
*A01H 6/42* (2018.01)

(52) U.S. Cl.
USPC ..... Plt./327
CPC ..... *A01H 6/425* (2018.05); *A01H 5/02* (2013.01)

(58) Field of Classification Search
USPC ..... Plt./327
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PECZ0020' particularly distinguished salmon colored inflorescences with large fully double round florets, held above medium green zoned foliage, on a medium vigorous mounding plant.

1 Drawing Sheet

Latin name of the genus and species of the plant claimed: *Pelargonium* x *hortorum*.

Varietal denomination: 'PECZ0020'.

BACKGROUND OF THE NEW PLANT

The present invention comprises a new *Pelargonium*, botanically known as *Pelargonium* x *hortorum*, and hereinafter referred to by the variety name 'PECZ0020'.

'PECZ0020' is a product of a planned breeding program. The new cultivar 'PECZ0020' has salmon colored inflorescences with large fully double round florets, held above medium green zoned foliage, on a medium vigorous mounding plant.

'PECZ0020' originates from a self-pollination in a controlled breeding program made in July 2012, in a greenhouse in Enkhuizen, The Netherlands. The parent was an unpatented plant of *Pelargonium* x *hortorum* parentage identified as 'PEZ-AZ3310-04' with lighter green foliage and more single flowered florets and larger plant habit when compared to 'PECZ0020'.

'PECZ0020' was selected as one flowering plant within the progeny of the stated cross in May 2013 in a greenhouse in Enkhuizen.

The first act of asexual reproduction of 'PECZ0020' was accomplished when vegetative cuttings were propagated from the initial selection in May 2013 in a greenhouse in Enkhuizen, The Netherlands.

BRIEF SUMMARY OF INVENTION

Horticultural examination of plants grown from cuttings of the plant initiated in May 2013 in Enkhuizen, The Netherlands and continuing thereafter, has demonstrated that the combination of characteristics as herein disclosed for 'PECZ0020' are firmly fixed and are retained through successive generations of asexual reproduction.

'PECZ0020' has not been observed under all possible environmental conditions. The phenotype may vary significantly with variations in environment such as temperature, light intensity, and day length.

A Plant Breeder's Right for this cultivar was applied for in the European Union on Feb. 3, 2020, No. 2020/0358. 'PECZ0020' has not been made publicly available prior to the effective filing date of this application, notwithstanding any disclosure that may have been made less than one year prior to the effective filing date of this application by the inventor or another who obtained 'PECZ0020' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PECZ0020' with colors being as true as possible with an illustration of this type.

Figure 1:
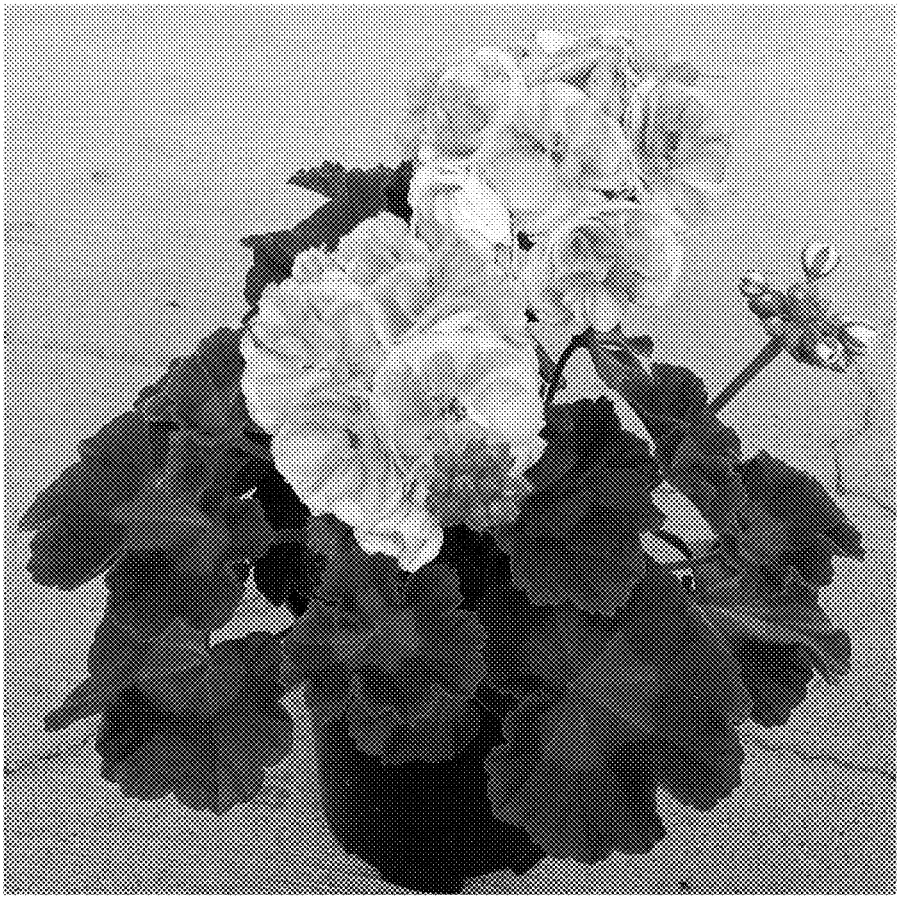
Figure 2:
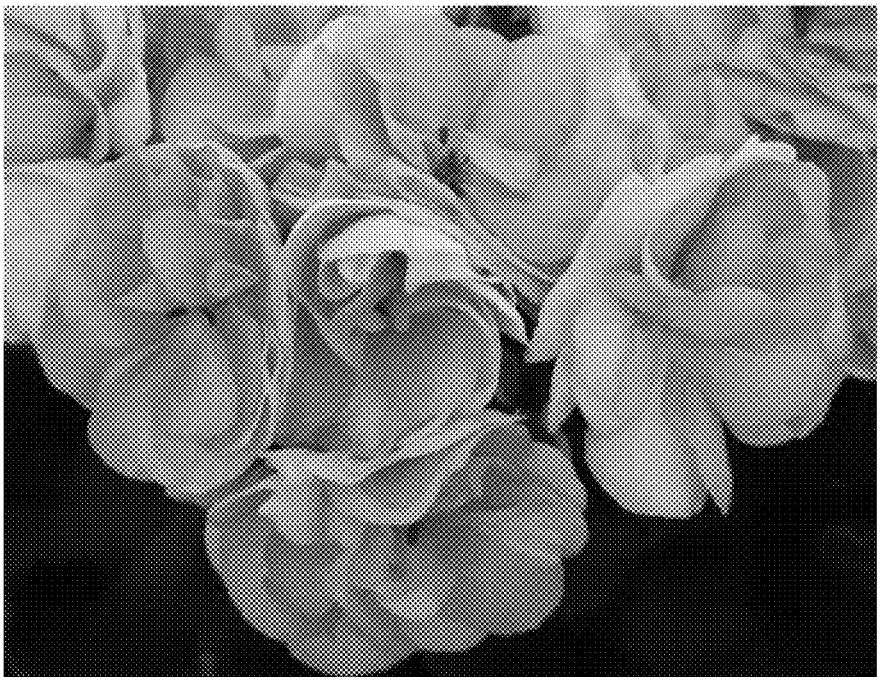

The photographic drawings show in FIG. 1, 1 flowering plant of the new variety and in FIG. 2, a close-up of an inflorescence.

DETAILED BOTANICAL DESCRIPTION

The plant descriptions and measurements were taken in The Netherlands mid-May 2020 under natural light. These plants were approximately 12 weeks old and were grown in a 12 cm pots, in a greenhouse trial. The plants shown in the photographs were about 12 weeks old growing in a 12 cm pot in a greenhouse. The photographs were taken in April 2020.

Color references are made to The Royal Horticultural Society Colour Chart (R.H.S.) 2001.

TABLE 1

DIFFERENCES BETWEEN THE NEW VARIETY 'PECZ0020' AND A MOST SIMILAR VARIETY

| | 'PECZ0020' | 'Pacsalkom' (U.S. Plant Pat. No. 20,673) |
|---|---|---|
| Leaf zonation pattern: | Visible under most conditions | Not discernible |
| Stigma color: | Red (RHS 51A) | Red-purple (RHS 60A) |
| Corolla color fading with age: | Fading to light-red (RHS 49D) | Fading to white (RHS 155D) |

Plant:

*Form, growth and habit.*—Upright, rounded growth habit.

*Plant height.*—17-20.0 cm.

*Plant height (inflorescence included).*—23-30.0 cm.

*Plant width.*—18-27.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Closest to RHS 137A, with distinct zonation pattern RHS 147A.

*Immature leaf, lower surface.*—Closest to RHS 137C.

*Mature leaf, color upper surface.*—Closest to RHS 137A, with distinct zonation pattern RHS 147A.

*Mature leaf, color lower surface.*—Closest to RHS 137C.

*Length.*—6-7 cm.

*Width.*—7-7.5 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—RHS 187A.

*Color of veins, upper surface.*—RHS 137C becoming indistinct.

*Color of veins, lower surface.*—RHS 137C becoming indistinct.

*Pattern of veining.*—Palmate.

*Petiole color.*—RHS 137C.

*Petiole length.*—5.5-7 cm.

*Diameter of petiole.*—0.2 cm.

*Texture.*—Pilose, hirsute, glandular hairs.

Stem:

*Quantity of branches.*—3-7.

*Color of stem.*—Between RHS 144A and RHS 144B.

*Length of stem.*—10-12.0 cm.

*Diameter.*—0.5 cm.

*Length of internodes.*—1-3 cm.

*Texture.*—Sparsely hirsute, pilose, glandular hairs.

Peduncle:

*Color of peduncle.*—RHS 137C.

*Length of peduncle.*—13-15.0 cm.

*Peduncle diameter.*—0.3-0.35 cm.

*Texture.*—Hirsute, glandular hairs.

Pedicel:

*Color of pedicel.*—RHS 144A to RHS 144B.

*Length of pedicel.*—2-3.5 cm.

*Diameter of pedicel.*—0.15-0.2 cm.

*Texture.*—Sparsely pilose, glandular hairs.

Bud (just before opening):

*Color.*—Closest to RHS 36D.

*Length.*—1.5 cm.

*Width.*—1.2-1.5 cm.

*Shape.*—Spherical.

Inflorescence:

*Type.*—Umbel; semi-spherical or nearly semi- spherical.

*Lastingness of individual flowers.*—7-9 days at 18° C. temperature.

*Number of inflorescences per plant.*—2-4, with 2-4 immature umbels in various stages.

*Fragrance.*—None.

*Umbel diameter.*—9-10 cm.

*Umbel depth.*—6.5-7.5 cm.

Corolla:

*Form.*—Double.

*Number of petals.*—15-40.

*Diameter of flower.*—4-5 cm.

*Depth of flower.*—1.3-1.7 cm.

*Color upper petals, upper surface.*—RHS 39B at edge with RHS 39C center, fading to close to RHS 49B.

*Color upper petals, lower surface.*—RHS 38D.

*Length of upper petals.*—1.9-2.5 cm.

*Width of upper petals.*—2-2.2 cm.

*Color lower petals, upper surface.*—RHS 39B at edge with RHS 39C center, fading to close to RHS 49B.

*Color lower petals, lower surface.*—RHS 38D.

*Length of lower petals.*—2-2.4 cm.

*Width of lower petals.*—2-2.6 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A mottled with anthocyanins of about RHS 178B.

*Length of sepals.*—1.2 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.1 cm.

*Style color.*—Close to RHS 51A.

*Style length.*—0.5-0.7 cm.

*Stigma color*.—Close to RHS 51A.

*Ovary color*.—RHS 144A mottled with anthocyanins of about RHS 178B.

*Ovary length*.—0.4-0.5 cm.

*Ovary diameter*.—0.2 cm.

Androecium:

*Number of stamens*.—5-7 with 1-4 staminoids.

*Color of filaments*.—RHS N155C with RHS 51B towards the apex.

*Length filaments*.—0.7-0.8 cm.

*Anther color*.—RHS 52C.

*Length of anthers*.—0.2-0.3 cm.

*Color of pollen*.—Close to RHS N172B.

*Pollen amount*.—Abundant.

*Fertility/seed set*.—Has not been determined to date.

*Disease/pest resistance*.—Has not been determined to date.

What is claimed is:

1. A new and distinct variety of *Pelargonium* plant named 'PECZ0020' substantially as illustrated and described herein.

* * * * *